(12) United States Patent
Choi et al.

(10) Patent No.: US 11,596,381 B2
(45) Date of Patent: Mar. 7, 2023

(54) MULTIPLE FREQUENCY SCANNING USING AN ULTRASOUND PROBE

(71) Applicant: Verathon Inc., Bothell, WA (US)

(72) Inventors: Joon Hwan Choi, Bothell, WA (US); Fuxing Yang, Bothell, WA (US)

(73) Assignee: Verathon Inc., Bothell, WA (US)

( * ) Notice: Subject to any disclaimer, the term of this patent is extended or adjusted under 35 U.S.C. 154(b) by 230 days.

(21) Appl. No.: 16/287,088

(22) Filed: Feb. 27, 2019

(65) Prior Publication Data

US 2019/0282200 A1    Sep. 19, 2019

Related U.S. Application Data

(60) Provisional application No. 62/644,773, filed on Mar. 19, 2018.

(51) Int. Cl.
*A61B 8/08* (2006.01)
*A61B 8/14* (2006.01)
*A61B 8/00* (2006.01)
*A61B 5/00* (2006.01)

(52) U.S. Cl.
CPC ............ *A61B 8/0833* (2013.01); *A61B 5/726* (2013.01); *A61B 5/7257* (2013.01); *A61B 5/7267* (2013.01); *A61B 8/14* (2013.01); *A61B 8/5207* (2013.01); *A61B 8/54* (2013.01)

(58) Field of Classification Search
CPC ... A61B 8/0833; A61B 8/7253; A61B 8/7257; A61B 8/726; A61B 8/7267; A61B 8/5207; A61B 8/54; A61B 8/5223; A61B 5/7267; G01S 7/52039; G01S 15/8915
See application file for complete search history.

(56) References Cited

U.S. PATENT DOCUMENTS

| 4,689,986 A | 9/1987 | Carson et al. |
| 5,259,386 A | 11/1993 | Sharkawy |
| 5,363,852 A | 11/1994 | Sharkawy |
| 5,941,825 A | 8/1999 | Lang et al. |
| 5,961,460 A | 10/1999 | Guracar et al. |
| 6,045,505 A | 4/2000 | Holley et al. |
| 6,050,944 A | 4/2000 | Holley et al. |

(Continued)

FOREIGN PATENT DOCUMENTS

WO    WO-2012155153 A1 * 11/2012 ........... A61B 8/0825

*Primary Examiner* — Joel Lamprecht
*Assistant Examiner* — Nyrobi Celestine
(74) *Attorney, Agent, or Firm* — Snyder, Clark, Lesch & Chung, LLP

(57) ABSTRACT

A system may include an ultrasound probe and a controller unit configured to communicate with the ultrasound probe. The controller unit may be further configured to transmit ultrasound signals using the ultrasound probe toward an area of interest in a patient's body, wherein the ultrasound signals include a fundamental frequency signal and at least one harmonic frequency signal; receive echo signals from the area of interest based on the transmitted ultrasound signals; obtain a fundamental frequency echo signal and at least one harmonic frequency echo signal from the received echo signals; and generate a visual representation of the area of interest based on the obtained fundamental frequency echo signal and the obtained at least one harmonic frequency echo signal.

19 Claims, 13 Drawing Sheets

(56) References Cited

U.S. PATENT DOCUMENTS

| | | | |
|---|---|---|---|
| 6,108,572 A * | 8/2000 | Panda | A61B 8/06 600/407 |
| 6,132,374 A * | 10/2000 | Hossack | A61B 8/00 600/443 |
| 6,344,023 B1 | 2/2002 | Fukukita et al. | |
| 6,425,869 B1 * | 7/2002 | Rafter | A61B 8/4281 600/458 |
| 6,494,097 B1 | 12/2002 | Shihadeh | |
| 7,540,842 B2 | 6/2009 | Napolitano et al. | |
| 7,604,600 B2 * | 10/2009 | Umemura | A61B 8/481 600/437 |
| 7,753,847 B2 | 7/2010 | Greenleaf et al. | |
| 8,167,803 B2 * | 5/2012 | McMorrow | G01S 7/52038 600/437 |
| 8,419,643 B2 | 4/2013 | Sarvazyan | |
| 8,454,516 B1 * | 6/2013 | Roundhill | A61B 8/463 600/447 |
| 8,485,974 B2 | 7/2013 | Liu et al. | |
| 8,679,019 B2 | 3/2014 | Jurvelin et al. | |
| 8,740,799 B2 * | 6/2014 | Itani | G01S 15/8959 600/458 |
| 8,834,376 B2 | 9/2014 | Stergiopoulos et al. | |
| 9,042,963 B2 | 5/2015 | Iddan | |
| 9,737,281 B2 * | 8/2017 | Taniguchi | A61B 8/5207 |
| 10,952,703 B2 * | 3/2021 | Adams | A61B 8/4488 |
| 2004/0064043 A1 | 4/2004 | Rielly et al. | |
| 2006/0052699 A1 * | 3/2006 | Angelsen | A61B 8/483 600/437 |
| 2007/0038094 A1 | 2/2007 | Kruglikov | |
| 2007/0038095 A1 | 2/2007 | Greenleaf et al. | |
| 2008/0125653 A1 | 5/2008 | Antich et al. | |
| 2009/0062644 A1 | 3/2009 | Mcmorrow et al. | |
| 2009/0264757 A1 * | 10/2009 | Yang | G01S 7/52082 600/443 |
| 2014/0180078 A1 | 6/2014 | Nair | |
| 2014/0276049 A1 | 9/2014 | Doherty et al. | |
| 2014/0371587 A1 | 12/2014 | Vanderby et al. | |
| 2015/0196281 A1 * | 7/2015 | Takagi | A61B 8/06 600/408 |
| 2018/0214122 A1 * | 8/2018 | Ansell | A61B 5/204 |
| 2020/0364854 A1 * | 11/2020 | Fedewa | G06T 7/0012 |

* cited by examiner

MULTIPLE FREQUENCY SCANNING USING AN ULTRASOUND PROBE

PRIORITY INFORMATION

This patent application claims benefit of priority to U.S. Provisional Application No. 62/644,773, entitled "MULTIPLE FREQUENCY SCANNING USING AN ULTRASOUND PROBE" and filed on Mar. 19, 2018, which is hereby incorporated herein by reference in its entirety.

BACKGROUND INFORMATION

An ultrasound probe may generate ultrasound signals using a transducer, such as, for example, a piezoelectric transducer or a capacitive transducer, which converts electrical signals into ultrasound energy and which converts ultrasound echoes back into electrical signals. Ultrasound probes are typically used to identify a target organ or other structures in the body and/or determine features associated with the target organ/structure, such as the size of the organ/structure or the volume of fluid in the organ. Different types of ultrasound signals may generate different types of echo signals from particular structures in the body. Therefore, different types of ultrasound signals may be used to identify different structures in the body.

DETAILED DESCRIPTION OF PREFERRED EMBODIMENTS

Figure 1A:
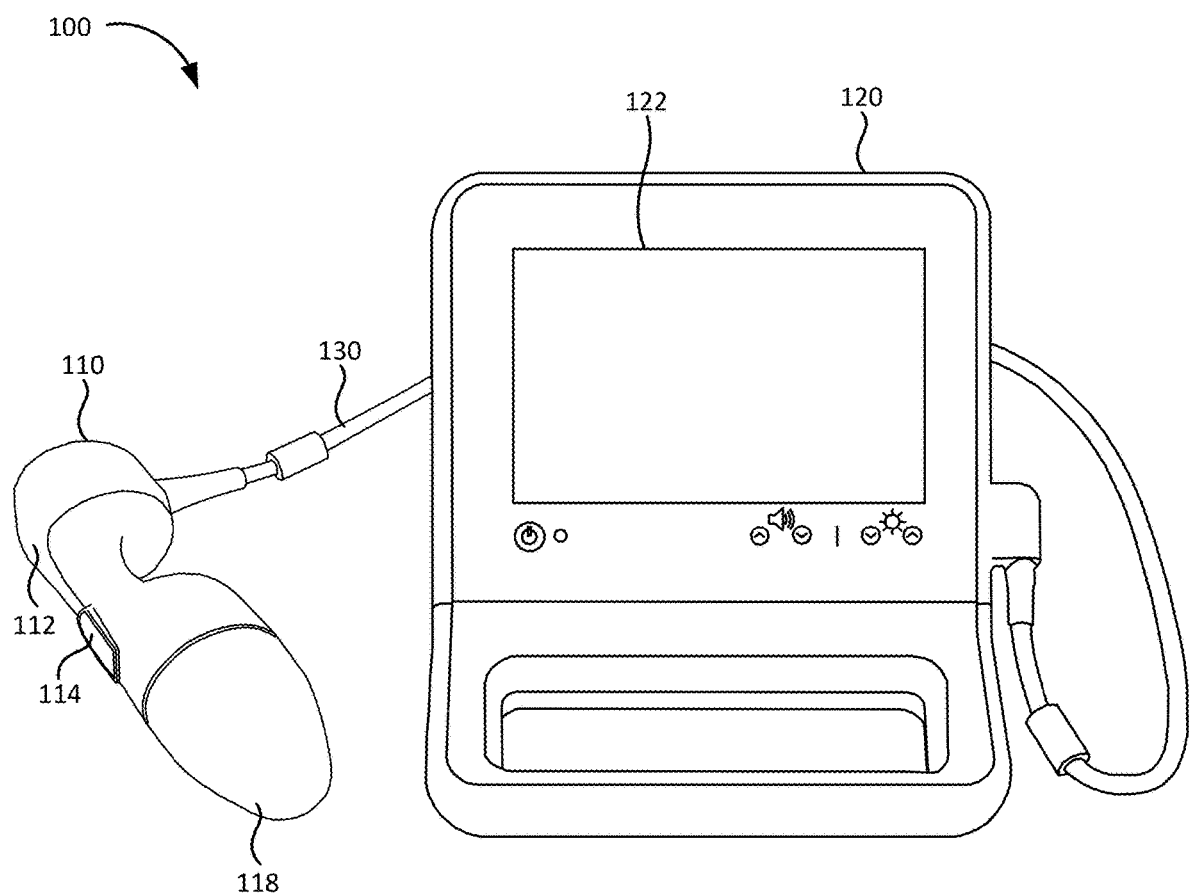
FIG. 1A is a diagram illustrating an exemplary ultrasound system according to an implementation described herein.

The following detailed description refers to the accompanying drawings. The same reference numbers in different drawings identify the same or similar elements.

An ultrasound probe may transmit a pulse at a particular frequency, such a pulse at 2.5 megahertz (MHz), 5.0 MHz, and/or another frequency, toward an area of interest in a patient's body. The ultrasound signals may echo (i.e., reflect) off tissues in the area of interest and echo signals may be received by the ultrasound probe and processed to generate images and/or characterize the area of interest. As a result of non-linear propagation through bodily tissues, the echo signals may include echo signals at the fundamental frequency and echo signals at one or more harmonic frequencies of the fundamental frequency. The harmonic frequency signals may be used to characterize the area of interest by, for example, determining a boundary of a body structure, identifying an area that includes fluid, distinguish one body organ from another body organ, etc.

For example, body tissue may respond differently to ultrasound pulses than fluid with respect to nonlinear propagation. Nonlinear propagation may result in generation of harmonic frequencies components and the extent of generation of harmonic frequencies may be used, for example, to identify a type of body tissue in a particular region of the area of interest. One parameter used to determine the importance of nonlinear or dissipative behavior (e.g., attenuation) is the Goldberg number. The Goldberg number is a dimensionless number defined as the ratio between the absorption length $l_a$ (the inverse of the absorption coefficient) and shock length $l_s$, which is a measure of the length at which a waveform would shock (i.e., move faster than the local wave propagation speed) if no absorption is present. The Goldberg number $\Gamma$ may expressed as:

$$\Gamma = \frac{l_a}{l_s} = \frac{k\beta M}{\alpha} \qquad \text{Eq. (1)}$$

where k corresponds to the wave number, β corresponds to the acoustic Mach number, M corresponds to the acoustic nonlinearity parameter, and α corresponds to the absorption coefficient. However, the harmonic frequency components in the echo signals may not always be of sufficiently high amplitude to satisfactorily characterize the area of interest.

Implementations described herein relate to multiple frequency scanning using an ultrasound probe. An ultrasound system may be configured to control an ultrasound transducer to transmit ultrasound signals at multiple frequencies. For example, the ultrasound system may transmit ultrasound signals at a fundamental frequency and at one or more harmonic frequencies of the fundamental frequency. When the ultrasound transducer transmits multiple frequencies that include harmonic frequencies in addition to a fundamental frequency, measures of nonlinearity such as the Goldberg number may not be the distinguishing factor between different structures, such as tissues and fluid, because the harmonic frequency components of the echo signals may not be generated by nonlinear propagation through the structures in the area of interest in the patient's body. Nevertheless, different harmonic frequency components of the echo signals may provide information relating to frequency-dependent attenuation. Furthermore, because harmonic frequency signals are being transmitted by the ultrasound transducer, rather than being generated by nonlinear propagation in the body structures, the frequency-dependent attenuation may be measured more clearly due to the higher amplitude of the harmonic frequency components in the echo signals.

The ultrasound system may be configured to transmit ultrasound signals, which include a fundamental frequency signal and at least one harmonic frequency, using an ultrasound probe toward an area of interest in a patient's body; receive echo signals from the area of interest based on the transmitted ultrasound signals; obtain a fundamental frequency echo signal and at least one harmonic frequency echo signal from the received echo signals; and generate a visual representation of the area of interest based on the obtained fundamental frequency echo signal and the obtained at least one harmonic frequency echo signal.

In some implementations, multiple frequencies may be transmitted in a multi-frequency manner (e.g., simultaneously), such as, for example, transmitting an ultrasound pulse that includes a 2.5 MHz component and a 5.0 MHz component. In other implementations, multiple frequencies may be transmitted in a variable-frequency manner (e.g., sequentially or alternately), such as, for example, transmitting 2.5 MHz and 5.0 MHz pulses alternately. In yet other implementation, multiple frequencies may be transmitted both simultaneously and sequentially, such as, for example, alternating transmitting 1 and 2 MHz pulses together, and transmitting 4 and 6 MHz pulses together.

In yet other implementations, the ultrasound system may be configured to control the ultrasound probe to transmit and/or receive broadband ultrasound signals. For example, an ultrasound transducer may transmit a broadband pulse that covers the range from 2 MHz to 4 MHz and receives returned echoes in a range from 2 MHz to 4 MHz, returned echoes in a range from 2 MHz to 8 MHz, and/or returned echoes in a different range. One or more bandpass filters may be applied to the received broadband echoes to retrieve echo signals at particular frequencies. For example, in some implementations, a Short-Time Fourier Transform (STFT) operation, a Wavelet Decomposition (WD), a Wavelet Packet Decomposition (WPD) operation, and/or another type of signal processing operation may be used to retrieve frequency component echo signals from a signal of returned echoes. As an example, a 128-tap STFT unit may be configured to function as a filter bank that generates echo signal components at 128 different frequencies.

In yet other implementations, the ultrasound system may be configured to control the ultrasound probe to transmit and/or receive harmonic frequencies that are not integer multiples of the fundamental frequency. For example, rather than transmitting an ultrasound pulse at a 2 MHz fundamental frequency and harmonic frequencies at 4, 6, or 8 MHz, the ultrasound transducer may be controlled to transmit an ultrasound pulse at a 2 MHz fundamental frequency and ultrasound pulses at one or more non-integer harmonic frequencies, such as, for example, at 3 MHz, 5 MHz, and/or another non-integer harmonic frequency. Furthermore, one or more bandpass filters may be used to retrieve echo signals at one or more non-integer harmonic frequencies from returned echo signals based on the transmitted ultrasound pulses.

In some implementations, the harmonic frequency components retrieved from the returned echo signals may be used to generate an ultrasound image. As an example, an ultrasound image may be generated in which brightness/shade of a particular pixel represents the amplitude of a particular harmonic frequency echo signal at the location represented by the particular pixel. As another example, one or more parameters may be computed relating the fundamental frequency echo signal and a harmonic frequency echo signal, relating a first harmonic frequency echo signal and a second harmonic frequency echo signal, relating three or more frequency components, etc., and an ultrasound image may be generated based on the computed one or more parameters, in which the brightness/shade of a particular pixel represents a computed parameter at the location represented by the particular pixel. The computed parameters may include a power ratio (e.g., an attenuation ratio), attenuation coefficient, a probability value (e.g., indicating a likelihood of a pixel corresponding to a particular type of tissue, fluid, etc.), and/or another type of parameter. Thus, the ultrasound system may generate a series of ultrasound images for different harmonic frequency echo signals and/or different computed parameters, such as power ratios.

Furthermore, the ultrasound system may combine two or more of the generated ultrasound images. For example, the ultrasound system may generate a color map that assigns a particular color to a particular harmonic frequency echo signal and/or computed parameter, such as a power ratio. The brightness/shade of the assigned color at a particular pixel may correspond to the value of the particular harmonic frequency echo signal and/or computed parameter associated with the assigned color at the location represented by the particular pixel and multiple harmonic frequency echo signals and/or computed parameters may be displayed on the image using multiple colors.

Additionally or alternatively, the harmonic frequency components retrieved from the returned echo signals, and/or the computed parameters, may be used to characterize the area of interest by providing the harmonic frequency components and/or the computed parameter values as inputs into a classifier. The classifier may be trained to use the harmonic frequency components and/or the computed parameter values to distinguish between a first target and a second target in the area of interest (e.g., distinguish between a first body structure and a second body structure, etc.), to identify an area that includes a target in the area of interest (e.g., identify an area that includes fluid, etc.), or identify a target boundary in the area of interest (e.g., identify a tissue boundary, etc.), to identify a particular tissue and/or body structure, to identify a medical instrument (e.g., a catheter, needle, a cannula, etc.), to identify an ultrasound artifact, and/or to otherwise characterize the area of interest.

In some implementations, the generated ultrasound images may correspond to B-mode ultrasound images. In other implementations, other types of ultrasound images may be generated, such as probability mode (P-mode) ultrasound images. A P-mode ultrasound image may correspond to an ultrasound image (e.g., a B-mode ultrasound image, etc.) in which each particular pixel is mapped to a probability indicating whether that particular pixel is within or part of a target organ/structure. As another example, the generated ultrasound images may include Doppler mode ultrasound images (e.g., Power Doppler, Continuous Wave Doppler, Pulsed Wave Doppler, etc.), motion mode (M-mode) ultrasound images, and/or any other type of imaging modality that uses ultrasound data.

Furthermore, in other implementations, the harmonic frequency echo signal ultrasound images may be used for additional types of processing. As an example, the harmonic frequency echo signal ultrasound images may be used in connection with positioning a needle guide for needle insertion (e.g., to obtain a biopsy sample, etc.); to measure the volume of an area of interest (e.g., bladder volume measurement, prostate volume measurement, uterus volume measurement, aorta volume measurement, etc.); and/or to perform other types of processing.

FIG. 1A is a diagram illustrating an exemplary ultrasound system 100 according to an implementation described herein. As shown in FIG. 1A, ultrasound system 100 may include an ultrasound probe 110, a base unit 120, and a cable 130.

Ultrasound probe 110 may house one or more ultrasound transducers configured to generate ultrasound energy at a particular frequency and/or pulse repetition rate and to receive reflected ultrasound energy (e.g., ultrasound echoes) and convert the reflected ultrasound energy into electrical signals. For example, in some implementations, ultrasound probe 110 may be configured to transmit ultrasound signals in a range that extends from approximately about two megahertz (MHz) to approximately 10 or more MHz (e.g., 18 MHz). In other implementations, ultrasound probe 110 may be configured to transmit ultrasound signals in a different range. Furthermore, ultrasound probe 110 may house one or more motors for controlling the movement of the ultrasound transducer.

Ultrasound probe 110 may include a handle 112, a trigger 114, and a dome 118 (also referred to as a "nose"). A user (e.g., a medical practitioner, etc.) may hold ultrasound probe 110 via handle 112 and press trigger 114 to activate one or more ultrasound transceivers and transducers located in dome 118 to transmit ultrasound signals toward a patient's area of interest (e.g., a particular body organ, a body joint, a blood vessel, etc.). For example, probe 110 may be positioned on a pelvic area of a patient and over the patient's bladder.

Handle 112 enables a user to move probe 110 relative to a patient's area of interest. Activation of trigger 114 initiates an ultrasound scan of a selected anatomical portion while dome 118 is in contact with a surface portion of a patient's body when the patient's area of interest is scanned. Dome 118 may enclose one or more ultrasound transducers and may be formed from a material that provides an appropriate acoustical impedance match to the anatomical portion and/or permits ultrasound energy to be properly focused as it is projected into the anatomical portion. Dome 118 may also include transceiver circuitry that includes a transmitter and a receiver to transmit and receive ultrasound signals. Probe 110 may communicate with base unit 120 via a wired connection, such as via cable 130. In other implementations, probe 110 may communicate with base unit 120 via a wireless connection (e.g., Bluetooth, WiFi, etc.).

Base unit 120 may house and include one or more processors or processing logic configured to process reflected ultrasound energy that is received by probe 110 to produce an image of the scanned anatomical region. Furthermore, base unit 120 may include display 122 to enable a user to view images from an ultrasound scan, and/or to enable operational interaction with respect to the user during operation of probe 110. For example, display 122 may include an output display/screen, such as a liquid crystal display (LCD), light emitting diode (LED) based display, touchscreen, and/or another type of display that provides text and/or image data to a user.

For example, display 122 may provide instructions for positioning probe 110 relative to a selected anatomical portion of a patient. Alternatively, ultrasound probe 110 may include a small display (e.g., in handle 112) that provides instructions for positioning ultrasound probe 110. Display 122 may also display two-dimensional or three-dimensional images of the selected anatomical region. In some implementations, display 122 may include a graphical user interface (GUI) that allows the user to select various features associated with an ultrasound scan. For example, display 122 may include selection items (e.g., buttons, dropdown menu items, checkboxes, etc.) to select particular transmission frequencies. As an example, the selection items may enable the user to select a particular fundamental frequency, one or more integer harmonic frequencies, and/or one or more non-integer harmonic frequencies. As another example, the selection items may enable the user to select a broadband transmission signal.

Furthermore, display 122 may include selection items to select one or more harmonic frequency echo signals that are to be extracted from returned echo signals and/or to select one or more parameters (e.g., power/attenuation ratios, etc.) that are to be computed based on the returned echo signals. Moreover, display 122 may include selection items to select to use a classifier and to select a particular characterization to be performed by the classifier (e.g., organ identification, fluid detection, tissue boundary detection, etc.).

Additionally, display 122 may include selection items to select particular types of ultrasound images to be obtained, such as B-mode images, P-mode images, Doppler ultrasound images, harmonic mode images, M-mode images, and/or other types of ultrasound images. Moreover, display 122 may include selection items to select an aiming mode for probe 110 and/or to initiate a three-dimensional (3D) scan after probe 110 has been successfully positioned with respect to the patient's area of interest.

Figure 1B:
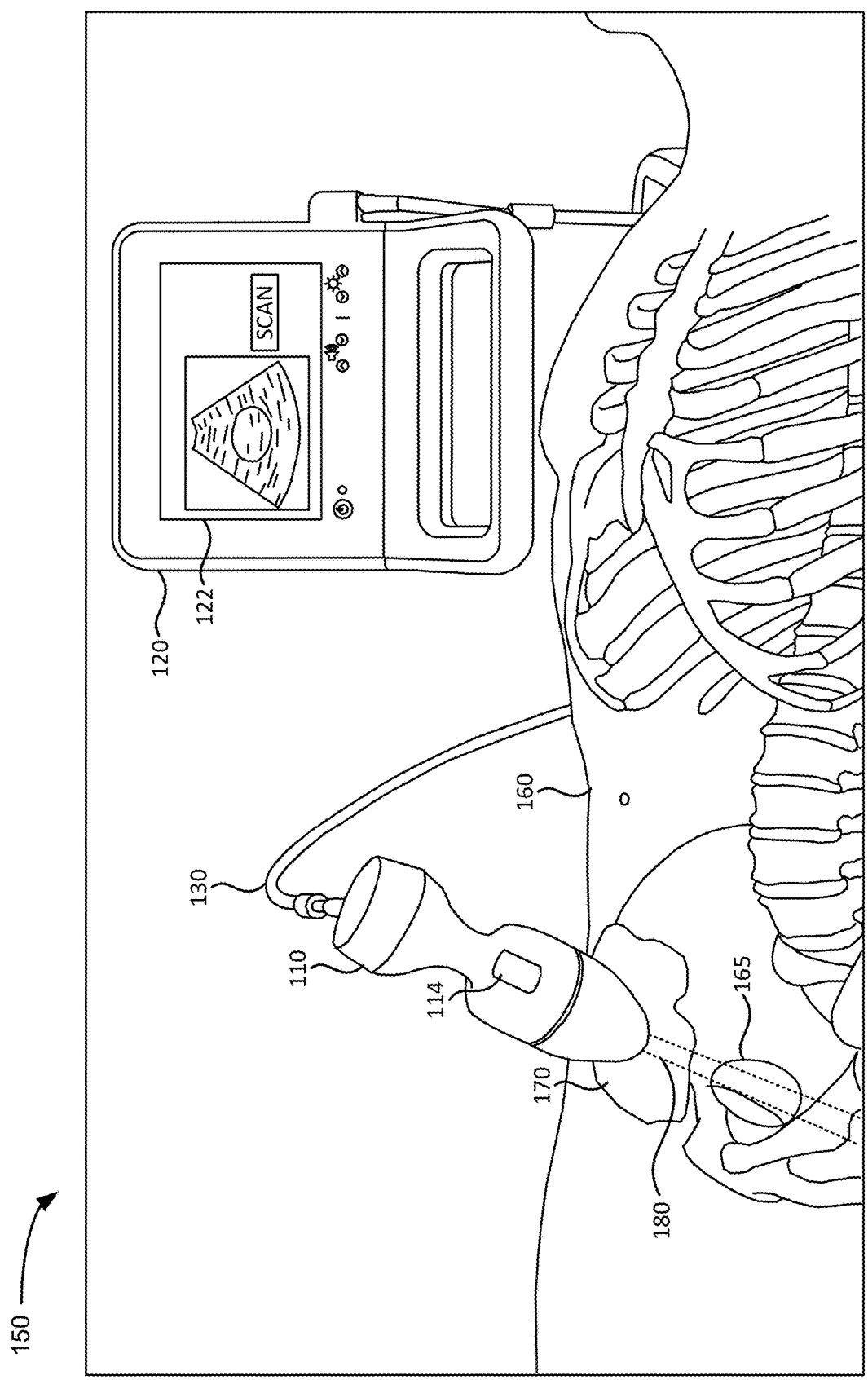
FIG. 1B is a diagram illustrating an exemplary environment for the ultrasound system of FIG. 1A according to an implementation described herein.

FIG. 1B is a diagram illustrating an exemplary environment 150 for ultrasound system 100 according to an implementation described herein. Environment 150 illustrates the operation of ultrasound system 100 with respect to a patient 160. As shown in FIG. 1B, patient 160 may be positioned so that a patient's area of interest may be scanned. For example, assume the area of interest corresponds to the patient's bladder 165. To scan bladder 165, ultrasound probe 110 may be positioned against a surface portion of patient 160 that is proximate to the anatomical portion to be scanned. The user may apply acoustic gel 170 (or gel pads) to the skin of patient 160 over the area of bladder 165 to provide an acoustical impedance match when dome 118 is placed against the skin.

The user may select an aiming mode via base unit 120 (e.g., by selecting an aiming mode button, menu item, etc., on display 122, by speaking a voice command, etc.). Alternatively, an aiming mode may be selected automatically when base unit 120 detects motion of ultrasound probe 110 or ultrasound probe 110 contacts acoustic gel 170 or the skin of patient 160 (e.g., via an accelerometer and/or gyroscope inside ultrasound probe 110). Ultrasound probe 110 may transmit ultrasound signals 180 through bladder 165 and may receive reflected ultrasound signals. The reflected ultrasound signals may be processed into images that are displayed on display 122.

Although FIGS. 1A and 1B show exemplary components of ultrasound system 100, in other implementations, ultrasound system 100 may include fewer components, different components, additional components, or differently arranged components than depicted in FIGS. 1A and 1B. Additionally or alternatively, one or more components of ultrasound system 100 may perform one or more tasks described as being performed by one or more other components of ultrasound system 100.

For example, in other embodiments, ultrasound probe 110 may correspond to a self-contained device that includes a microprocessor housed within ultrasound probe 110, configured to operably control the one or more ultrasound transducers, and to process the reflected ultrasound energy to generate ultrasound images. Accordingly, a display on ultrasound probe 110 may be used to display the generated images and/or to view other information associated with the operation of ultrasound probe 110. In yet other implementations, ultrasound probe 110 may be coupled to a general-purpose computer, such as a laptop, tablet, and/or a desktop computer (via a wired or wireless connection) that includes software that at least partially controls the operation of ultrasound probe 110 and/or that includes software to process information received from ultrasound probe 110 to generate ultrasound images.

Figure 2A:
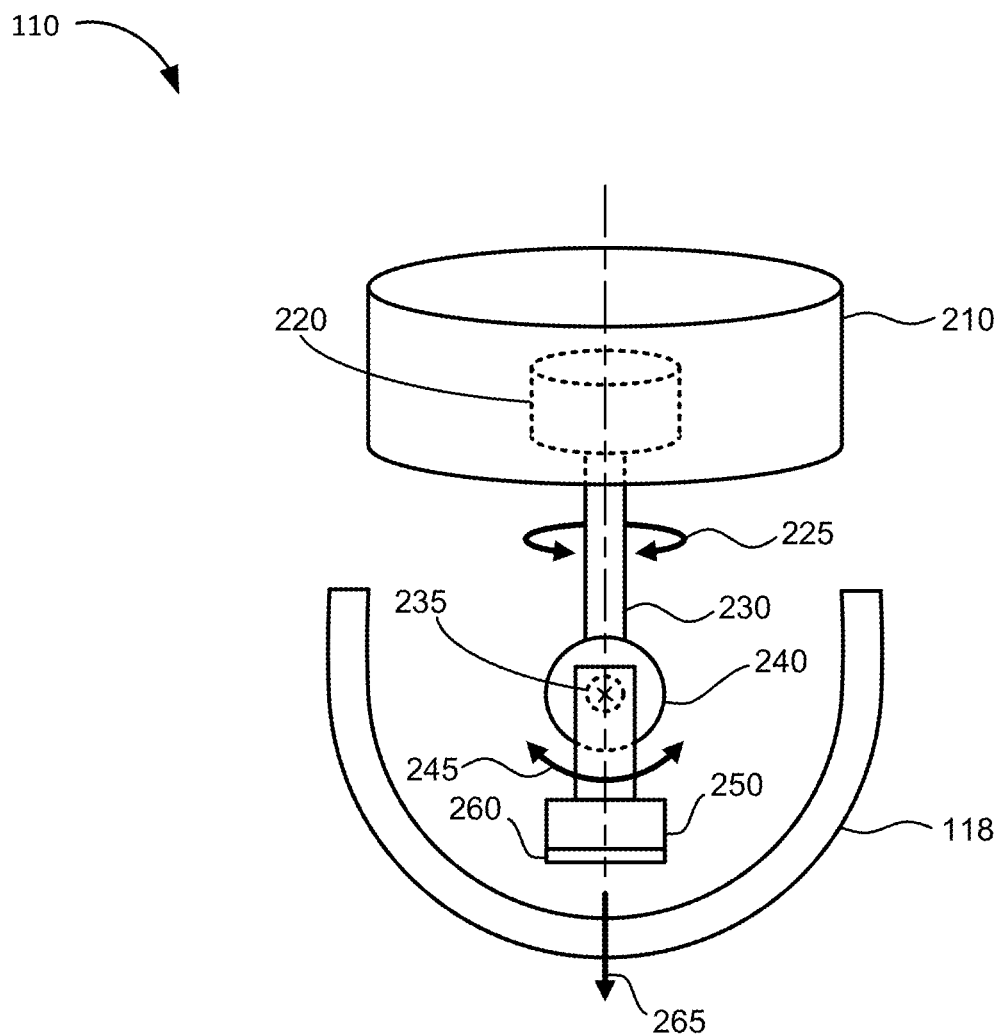
FIG. 2A is a diagram of a first exemplary ultrasound probe according to an implementation described herein.

FIG. 2A is a diagram of a first exemplary implementation of ultrasound probe 110 according to an implementation described herein. As shown in FIG. 2A, ultrasound probe 110 may include a single transducer element coupled to two rotational motors. In this implementation, ultrasound probe 110 may include a base 210 connected to dome 118, a theta motor 220, a spindle 230, a phi motor 240, and a transducer bucket 250 with a transducer 260. Theta motor 220, phi motor 240, and/or transducer 260 may include wired or wireless electrical connections that electrically connect theta motor 220, phi motor 240, and/or transducer 260 to base unit 120 via cable 130 (not shown in FIG. 2A).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in a longitudinal direction with respect to transducer 260, by rotating around a vertical axis referred to herein as a theta (θ) rotational plane 225. Spindle 230 may terminate in a shaft 235 and phi motor 240 may be mounted onto shaft 235. Phi motor 240 may rotate around an axis orthogonal to the theta rotational plane 225 around a horizontal axis referred to herein as a phi (φ)) rotational plane 245. Transducer bucket 250 may be mounted to phi motor 240 and may move with phi motor 240.

Transducer 260 may be mounted to transducer bucket 250. Transducer 260 may include a piezoelectric transducer, a capacitive transducer, and/or another type of ultrasound transducer. Transducer 260, along with transceiver circuitry associated with transducer 260, may convert electrical signals to ultrasound signals at a particular ultrasound frequency or range of ultrasound frequencies, may receive reflected ultrasound signals (e.g., echoes, etc.), and may convert the received ultrasound signals to electrical signals. As an example, transducer 260 may include a set of transducers, each of which is configured to generate an ultrasound pulse at a particular frequency. As another example, transducer 260 may include a broadband ultrasound transducer. Transducer 260 may transmit and receive ultrasound signals in a signal direction 265 that is substantially perpendicular to the surface of transducer 260.

Signal direction 265 may be controlled by the movement of phi motor 240 and the orientation of phi motor may be controlled by theta motor 220. For example, phi motor 240 may rotate back and forth across an angle that is less than 180 degrees to generate ultrasound image data for a particular plane and theta motor 220 may rotate to particular positions to obtain ultrasound image data for different planes.

In an aiming mode, theta motor 220 may remain stationary while phi motor 240 rotates back and forth to obtain ultrasound image data for a particular aiming plane. In the aiming mode, theta motor 220 may move back and forth between multiple aiming planes and phi motor 240 may rotate back and forth to obtain ultrasound image data. As an example, theta motor 220 may move between two orthogonal planes while the aiming mode is selected. As another example, theta motor 220 may sequentially rotate through three planes offset by 120 degrees to each other during the aiming mode.

In a 3D scan mode, theta motor 220 may cycle through a set of planes one or more times to obtain a full 3D scan of an area of interest. In each particular plane of the set of planes, phi motor 240 may rotate to obtain ultrasound image data for the particular plane. The movement of theta motor 220 and phi motor 240 may be interlaced in the 3D scan motor. For example, the movement of phi motor 240 in a first direction may be followed by a movement of theta motor 220 from a first plane to a second plane, followed by the movement of phi motor 240 in a second direction opposite to the first direction, followed by movement of theta motor 220 from the second plane to a third plane, etc. Such interlaced movement may enable ultrasound probe 110 to obtain smooth continuous volume scanning as well as improving the rate at which the scan data is obtained.

Figure 2B:
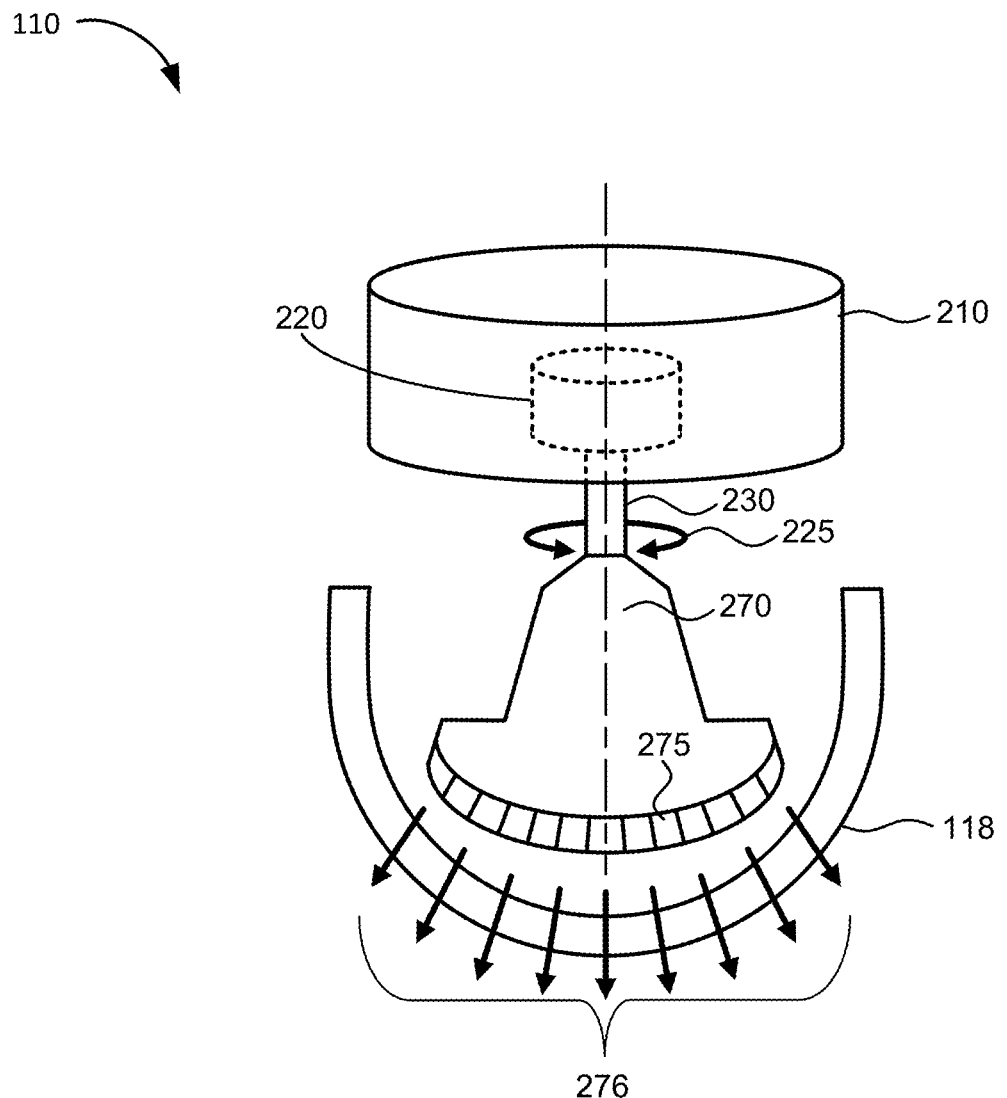
FIG. 2B is a diagram of a second exemplary ultrasound probe according to an implementation described herein.

FIG. 2B is a diagram of a second exemplary implementation of ultrasound probe 110 according to an implementation described herein. As shown in FIG. 2B, ultrasound probe 110 may include a one-dimensional (1D) array of transducer elements coupled to a rotation motor. In this implementation, ultrasound probe 110 may include a base 210 connected to dome 118, a theta motor 220, a spindle 230, and a transducer bucket 270 with a 1D transducer array 275. Theta motor 220 and/or 1D transducer array 275 may include wired or wireless electrical connections that electrically connect theta motor 220 and/or 1D transducer array 275 to base unit 120 via cable 130 (not shown in FIG. 2B).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in longitudinal direction with respect to 1D transducer array 275 by rotating around theta rotational plane 225. Spindle 230 may terminate in transducer bucket 270. 1D transducer array 275 may be mounted to transducer bucket 270. 1D transducer array 275 may include a curved 1D array of piezoelectric transducers, capacitive transducers, and/or other types of ultrasound transducers. 1D transducer array 275 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 1D transducer array 275 may transmit and receive ultrasound signals in a particular direction of a set of directions, illustrated as item 276 in FIG. 2B. Thus, together, the elements of 1D transducer array 275 may generate ultrasound image data for a particular plane.

In an aiming mode, theta motor 220 may remain stationary while 1D transducer array 275 obtains B-mode image data for a particular aiming plane. In the aiming mode, theta motor 220 may move back and forth between multiple aiming planes and 1D transducer array 275 may obtain ultrasound image data in each aiming plane. As an example, theta motor 220 may move between two orthogonal planes while aiming mode is selected. As another example, theta motor 220 may sequentially rotate through three planes located 120 degrees apart from each other. In a 3D scan mode, theta motor 220 may cycle through a set of planes one or more times to obtain a full 3D scan of an area of interest. In each particular plane of the set of planes, 1D transducer array 275 may obtain ultrasound image data for the particular plane.

Figure 2C:
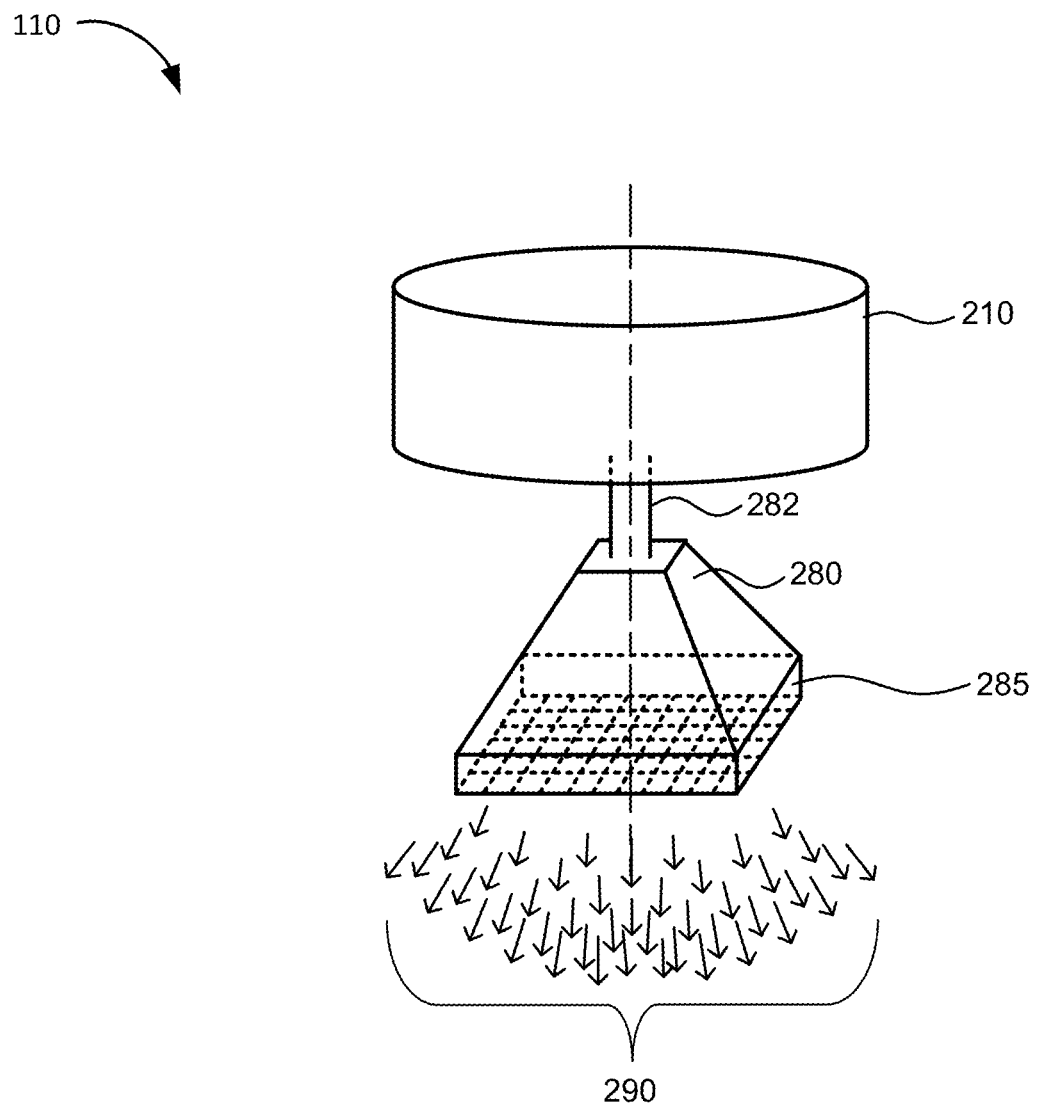
FIG. 2C is a diagram of a third exemplary ultrasound probe according to an implementation described herein.

FIG. 2C is a diagram of a third exemplary ultrasound probe 110 according to an implementation described herein. As shown in FIG. 2C, ultrasound probe 110 may include a two-dimensional (2D) array of transducer elements. In this implementation, ultrasound probe 110 may include a base 210, a spindle 230, and a transducer bucket 280 with a 2D transducer array 285. 2D transducer array 285 may include wired or wireless electrical connections that electrically connects 2D transducer array 285 to base unit 120 via cable 130 (not shown in FIG. 2C).

Base 210 may provide structural support to ultrasound probe 110 and secure spindle 230. Spindle 282 may terminate in transducer bucket 280. 2D transducer array 285 may be mounted to transducer bucket 280. 2D transducer array 285 may include a 2D array of piezoelectric transducers, capacitive transducers, and/or other types of ultrasound transducers. 2D transducer array 285 may convert electrical signals to ultrasound signals at a particular ultrasound frequency or range of ultrasound frequencies, may receive reflected ultrasound signals (e.g., echoes, etc.), and may convert the received ultrasound signals to electrical signals. Each element of 2D transducer array 285 may transmit and receive ultrasound signals in a particular direction of a set of directions, illustrated as item 290 in FIG. 2C. Thus, together, the elements of 2D transducer array 285 may generate ultrasound image data for multiple planes to generate a 3D ultrasound scan. In other words, 2D transducer array 285 may be controlled to tilt or direct an ultrasound beam/signal electronically in a particular direction.

In an aiming mode, 2D transducer array 285 may obtain ultrasound image data for one or more selected aiming planes. For a particular selected aiming plane, a subset of transducer elements from 2D transducer array 285 may be selected to generate an ultrasound image for the particular selected aiming plane. A particular plane may be scanned by using one or more rows of transducer elements in 2D transducer array 285. The number of rows may change dynamically depending on the target depth and the elevational focus may be electronically controlled by applying a timing delay between rows. As an example, two subsets of transducers may be selected for two orthogonal planes and may alternate between obtaining ultrasound images of the two orthogonal planes. Alternatively, the ultrasound images for the two orthogonal planes may be obtained substantially simultaneously. As another example, 2D transducer array 285 may cycle through three planes located 120 degrees apart from each other and three subsets of transducer elements from 2D transducer array 285 may obtain the ultrasound images for the three planes. In a 3D scan mode, 2D transducer array 285 may cycle through subsets of transducer elements one or more times to obtain a full 3D scan of an area of interest. Alternatively, multiple subsets of transducer elements, or even all of the transducer elements, of 2D transducer array 285 may be activated substantially simultaneously to obtain a full 3D scan of the area of interest.

Although FIGS. 2A, 2B, and 2C show exemplary components of ultrasound probe 110, in other implementations, ultrasound probe 110 may include fewer components, different components, additional components, or differently arranged components than depicted in FIGS. 2A, 2B, and 2C. Additionally or alternatively, one or more components of ultrasound probe 110 may perform one or more tasks described as being performed by one or more other components of ultrasound probe 110.

Figure 3:
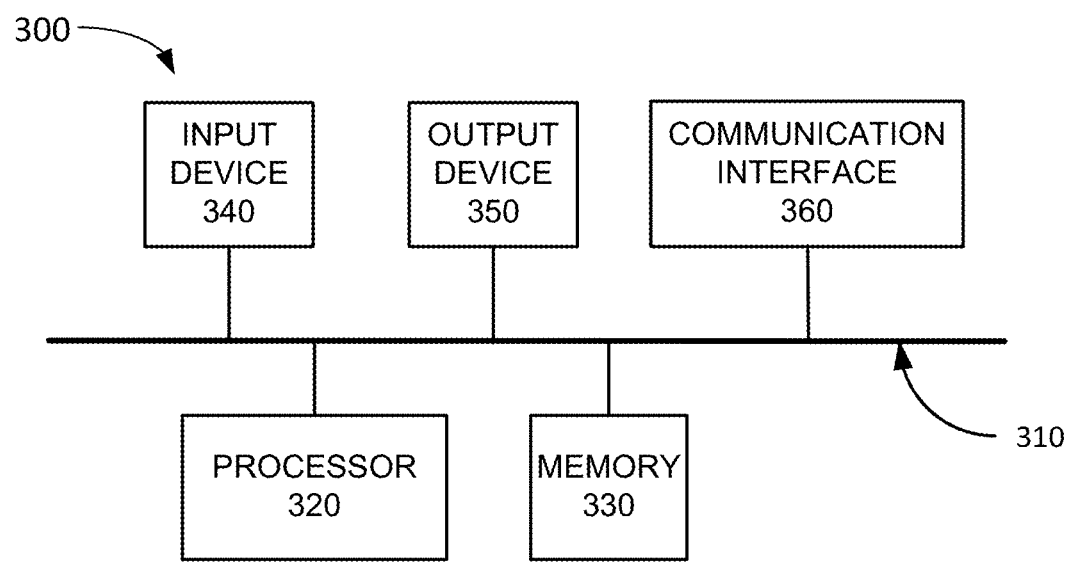
FIG. 3 is a diagram illustrating exemplary components of the controller unit of FIG. 1A.

FIG. 3 is a diagram illustrating example components of a device 300 according to an implementation described herein. Ultrasound probe 110 and/or base unit 120 may each include one or more devices 300. As shown in FIG. 3, device 300 may include a bus 310, a processor 320, a memory 330, an input device 340, an output device 350, and a communication interface 360.

Bus 310 may include a path that permits communication among the components of device 300. Processor 320 may include any type of single-core processor, multi-core processor, microprocessor, latch-based processor, and/or processing logic (or families of processors, microprocessors, and/or processing logics) that interprets and executes instructions. In other embodiments, processor 320 may include an application-specific integrated circuit (ASIC), a field-programmable gate array (FPGA), and/or another type of integrated circuit or processing logic.

Memory 330 may include any type of dynamic storage device that may store information and/or instructions, for execution by processor 320, and/or any type of non-volatile storage device that may store information for use by processor 320. For example, memory 330 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 340 may allow an operator to input information into device 300. Input device 340 may include, for example, a keyboard, a mouse, a pen, a microphone, a remote control, an audio capture device, an image and/or video capture device, a touch-screen display, and/or another type of input device. In some embodiments, device 300 may be managed remotely and may not include input device 340. In other words, device 300 may be "headless" and may not include a keyboard, for example.

Output device 350 may output information to an operator of device 300. Output device 350 may include a display, a printer, a speaker, and/or another type of output device. For example, device 300 may include a display, which may include a liquid-crystal display (LCD) for displaying content to the customer. In some embodiments, device 300 may be managed remotely and may not include output device 350. In other words, device 300 may be "headless" and may not include a display, for example.

Communication interface 360 may include a transceiver that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 360 may include a transmitter that converts baseband signals to radio frequency (RF) signals and/or a receiver that converts RF signals to baseband signals. Communication interface 360 may be coupled to an antenna for transmitting and receiving RF signals.

Communication interface 360 may include a logical component that includes input and/or output ports, input and/or output systems, and/or other input and output components that facilitate the transmission of data to other devices. For example, communication interface 360 may include a network interface card (e.g., Ethernet card) for wired communications and/or a wireless network interface (e.g., a WiFi) card for wireless communications. Communication interface 360 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 300 may perform certain operations relating to multi-frequency scanning using an ultrasound probe. Device 300 may perform these operations in response to processor 320 executing software instructions contained in a computer-readable medium, such as memory 330. A computer-readable medium may be defined as a non-transitory memory device. A memory device may be implemented within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of, or in combination with, software instructions to implement processes described herein. Thus, implementations described herein are not limited to any specific combination of hardware circuitry and software.

Although FIG. 3 shows exemplary components of device 300, in other implementations, device 300 may include fewer components, different components, additional components, or differently arranged components than depicted in FIG. 3. Additionally or alternatively, one or more components of device 300 may perform one or more tasks described as being performed by one or more other components of device 300.

Figure 4:
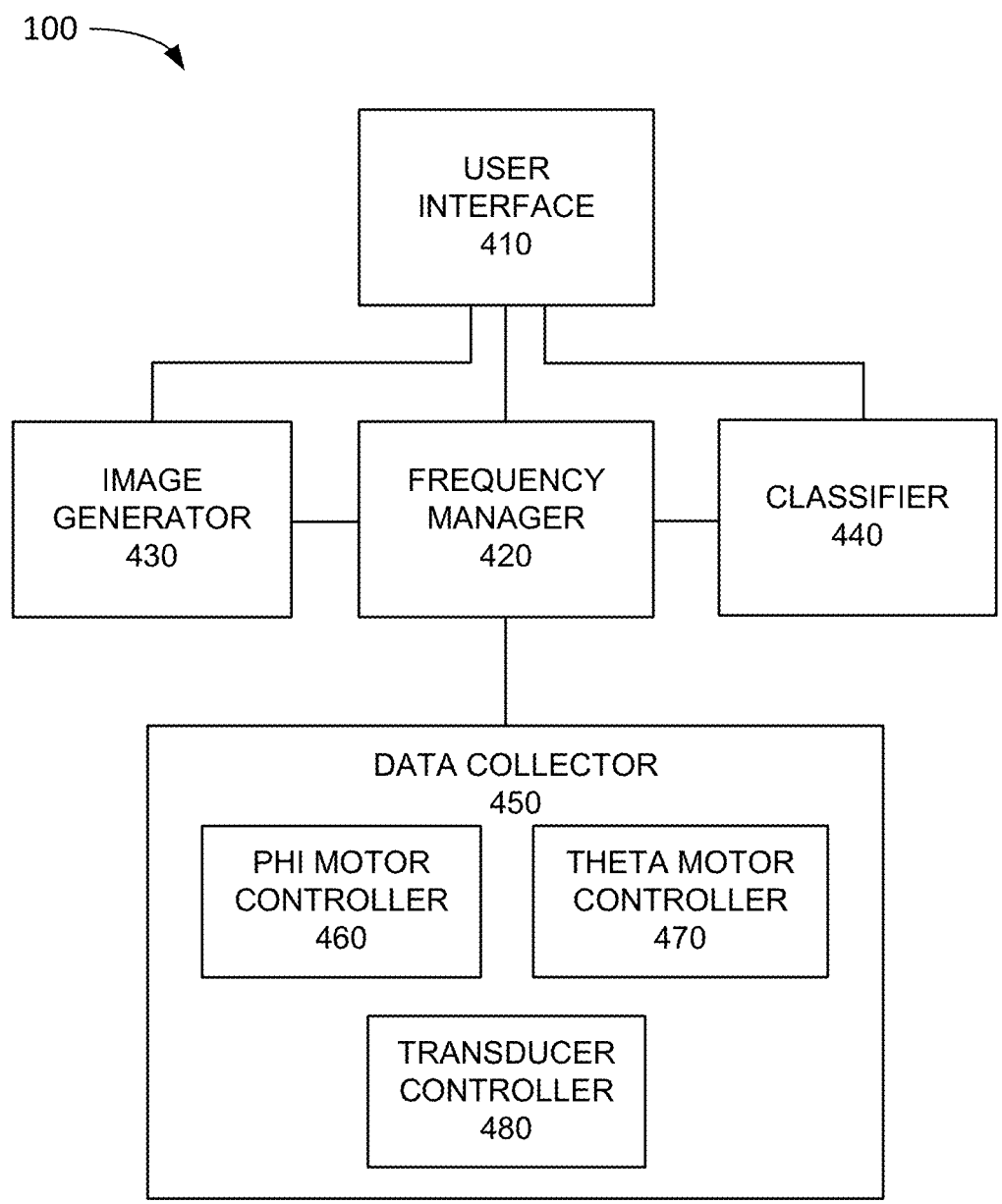
FIG. 4 is a diagram illustrating exemplary functional components of the system of FIG. 1A.

FIG. 4 is a diagram illustrating exemplary functional components of ultrasound system 100. The functional components of ultrasound system 100 may be implemented in ultrasound probe 110, base unit 120, and/or another device/system, for example, via processor 320 executing instructions from memory 330. Alternatively, some or all of the functional components of ultrasound system 100 may be implemented via hard-wired circuitry. As shown in FIG. 4, ultrasound system 100 may include a user interface 410, a frequency manager 420, an image generator 430, a classifier 440, and a data collector 450.

User interface 410 may generate a user interface (e.g., a graphical user interface) that displays ultrasound images to a user via display 122 and that is configured to receive selections and/or commands from the user via a touchscreen associated with display 122, via one or more control keys located on base unit 120 and/or on ultrasound probe 110, via a microphone included in base unit 120, and/or via another type of input method. For example, a user may select a type of ultrasound image, a set of transmission frequencies, a set of frequency components to be extracted from returned echo signals, whether to use a classifier to characterize the area of interest, a type of characterization to be performed by the classifier, and/or other types of selections relating to ultrasound scanning to be performed.

Frequency manager 420 may manage frequency components associated with ultrasound probe 110. Frequency manager 420 may select one or more transmission frequencies for transducer 260 (or transducer array 275 or 285). As an example, frequency manager 420 may select a fundamental frequency, one or more integer harmonic frequencies of the fundamental frequency, and/or one or more non-integer harmonic frequencies of the fundamental frequency. Furthermore, frequency manager 420 may select to transmit one or more harmonic frequencies simultaneously with the fundamental frequency and/or with each other, may select to transmit one or more harmonic frequencies alternatively with the fundamental frequency and/or with each other, and/or may select a combination of simultaneous and alternate transmission of harmonic frequencies. As another example, frequency manager 420 may select a broadband ultrasound transmission signal.

Furthermore, frequency manager 420 may select one or more harmonic frequency components to retrieve from returned ultrasound echo signals. For example, frequency manager 420 may select one or more bandpass filters, may select one or more outputs of an STFT or WPD function, and/or may otherwise select which harmonic frequency components are to be extracted from received echo signals. Moreover, frequency manager 420 may select to compute one or more parameters, such as power ratios, attenuation coefficients, P-mode values, etc., based on the harmonic frequency components retrieved from received echo signals. In some implementations, frequency manager 420 may provide the retrieved harmonic frequency components, and/or computed parameters, as inputs to classifier 440.

In some implementations, frequency manager 420 may select one or more transmission frequencies based on a user selection via, for example, user interface 410. In other implementations, frequency manager 420 may select one or more transmission frequencies, and/or one or more echo signal harmonic frequency components and/or power ratios to be computed, automatically (e.g., without user selection of transmission frequencies) based on one or more parameters, such as, for example, the particular area of interest to be scanned (e.g., organ, tissue, etc.), the type of ultrasound image selected, the type of classifier selected, and/or another type of parameter associated with an ultrasound scan.

Image generator 430 may generate ultrasound images based on received echo signals. For example, image generator 430 may instruct data collector 450 to obtain a particular type of ultrasound image, to move to a particular plane (e.g., a particular position of theta motor 220), and to generate an ultrasound image of a particular type for the particular plane (e.g., using phi motor 240 and transducer 260).

Classifier 440 may receive as input one or more harmonic frequency components and/or computed parameters and may output a classification output that characterizes the area of interest. For example, the classifier input may include one or more matrices of pixel values for an image generated based on particular harmonic frequency component and/or computed parameter. Classifier 440 may include a probabilistic classifier that outputs a probability value that a particular pixel corresponds to a particular structure, tissue, and/or fluid; a binary classifier that outputs a yes or no value for a particular pixel if the particular pixel is identified as belonging to a class (e.g., a particular organ, tissue, fluid, etc.); a multiclass classifier that outputs a particular value for a particular pixel indicating to which of a set of classes the particular pixel has been classified; and/or another type of classifier.

Classifier 440 may be implemented as a neural network classifier, a linear classifier, a naive Bayesian classifier, a kernel density estimation classifier, a decision tree classifier, a support vector machine classifier, a maximum entropy classifier, and/or another type of classifier. In some implementations, classifier 440 may be trained on a training set of images associated with predetermined classification output values (e.g., supervised learning). In other implementations, classifier 440 may be trained using a training set of images without predetermined classification (e.g., unsupervised learning).

Data collector 450 may be configured to collect ultrasound image data from ultrasound probe 110. Data collector 450 may include a phi motor controller 460, a theta motor controller 470, and a transducer controller 480. Phi motor controller 460 may control phi motor 240. Theta motor controller 470 may control theta motor 220. Transducer controller 480 may control transducer 260 (or 1D transducer array 275 or 2D transducer array 285).

Although FIG. 4 shows exemplary components of ultrasound system 100, in other implementations, ultrasound system 100 may include fewer components, different components, additional components, or differently arranged components than depicted in FIG. 4. Additionally or alternatively, one or more components of ultrasound system 100 may perform one or more tasks described as being performed by one or more other components of ultrasound system 100.

Figure 5:
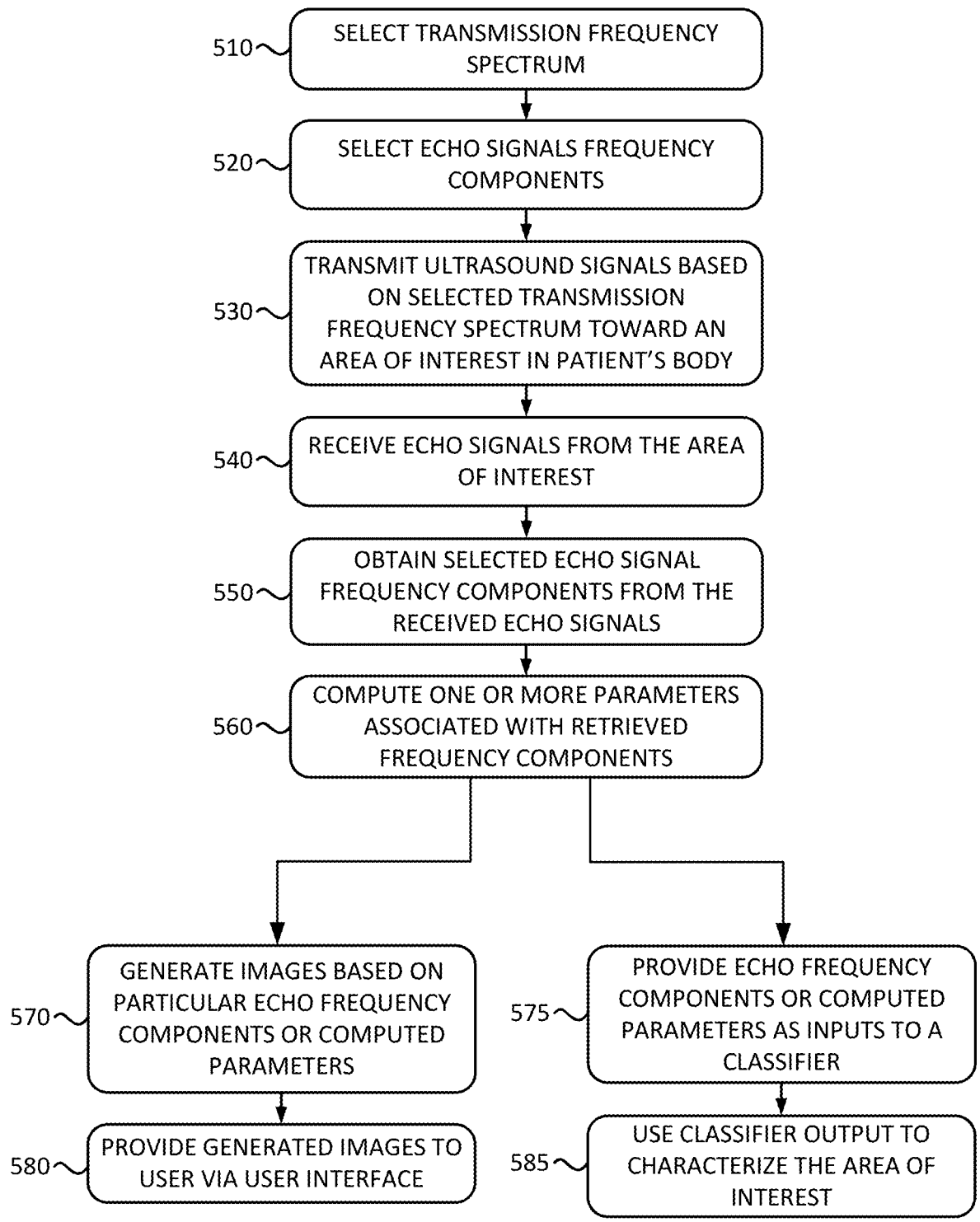
FIG. 5 is a flowchart of a process for multiple frequency ultrasound scanning according to an implementation described herein.

FIG. 5 is a flowchart of a process for multiple frequency ultrasound scanning according to an implementation described herein. In some implementations, the process of FIG. 5 may be performed by ultrasound system 100. In other implementations, some or all of the process of FIG. 5 may be performed by another device or a group of devices separate from ultrasound system 100.

The process of FIG. 5 may include selecting the transmission frequency spectrum (block 510). As an example, a user may select a particular fundamental frequency and one or more harmonics of the fundamental frequency as the transmission frequency spectrum. The one or more harmonics may include integer harmonics of the fundamental frequency and/or non-integer harmonics of the fundamental frequency. Furthermore, the user may select which harmonics are to be transmitted simultaneously with the fundamental frequency and/or with each other and which harmonics are to be transmitted alternatively. Thus, the user may specify a transmission sequence for the selected harmonics. As another example, the user may select to transmit a broadband pulse in a particular frequency range (e.g., from 2 MHz to 10 MHz, etc.). As yet another example, a user may select to transmit a particular set of harmonics alternating with a broadband pulse. In other implementations, a transmission frequency spectrum may be selected automatically (e.g., without user selection) based on one or more parameters, such as, for example, the particular area of interest, organ, or tissue to be scanned, the type of ultrasound image selected, the type of classifier selected, and/or another type of parameter associated with an ultrasound scan.

Echo signal frequency components may be selected (block 520). As an example, the user may select one or more harmonic frequency components to be extracted from the returned echo signals. For example, the user may specify one or more frequency ranges that are to be passed by a bandpass filter or output by a STFT or WPD function to generate the harmonic frequency components. In other implementations, the one or more harmonic frequency components may be selected automatically (e.g., without user selection) based on one or more parameters, such as, for example, the particular area of interest, organ, or tissue to be scanned, the type of ultrasound image selected, the type of classifier selected, and/or another type of parameter associated with an ultrasound scan. Additionally, one or more parameters to be computed may be selected, such as one or more power ratios, attenuation coefficients, P-mode values for a particular structure, organ, fluid, etc., and/or other types of parameters that may be derived from multi-frequency ultrasound data. For example, one or more power ratios may be selected to be computed (e.g., an attenuation ratio between the fundamental frequency and the first harmonic, an attenuation ratio between the fundamental frequency and a second harmonic, an attenuation ratio between the first harmonic and the second harmonic, etc.). Up to $n*(n-1)$ power ratios may be selected, where n corresponds to the number of frequency components selected to be retrieved.

Ultrasound signals based on the selected transmission frequency spectrum may be transmitted toward an area of interest in a patient's body (block 530). For example, data collector 450 may control transducer 260 to generate ultrasound pulses based on the selected transmission frequency spectrum. Echo signals from the area of interest may be received (block 540) and the selected echo signal frequency components may be obtained from the received echo signals (block 550). For example, frequency manager 420 may use a bandpass filter bank, an STFT or WPD function, and/or another technique to obtain the selected echo signal frequency components from the returned echo signals. One or more parameters associated with the obtained frequency components may be computed (block 560). For example, in some implementations, frequency manager 420 may compute one or more power ratios selected by the user or selected automatically. In other implementations, frequency manager 420 may compute attenuation coefficients, P-mode values (e.g., probability values that particular pixels correspond to a particular tissue, organ, fluid, etc.), a parameter that described a relationship between three or more frequency components (e.g., an average power or attenuation for three or more frequency components, etc.), and/or any other parameter that may be derived from multi-frequency ultrasound data.

Images based on particular echo frequency components or based on particular computed parameters may be generated (block 570) and provided to the user via a user interface (block 580). As an example, image generator 430 may generate an ultrasound image (e.g., a B-mode image) in which the brightness, intensity, or shade of a particular pixel represents the amplitude value for a retrieved frequency component at the location represented by the particular pixel. As another example, image generator 430 may generate an ultrasound image (e.g., a B-mode image) in which the brightness, intensity, or shade of a particular pixel represents the power ratio value between two retrieved frequency components at the location represented by the particular pixel. As yet another example, image generator 430 may generate an ultrasound image in which the brightness, intensity, or shade of a particular pixel represents a different type of computed parameter, such as computed attenuation coefficients, P-mode values, and/or any other type of parameter that may be derived from multi-frequency ultrasound data.

As yet another example, image generator 430 may combine two or more of the generated ultrasound images to generate a color map. The color map may assign a particular color to a particular harmonic frequency echo signal and/or a particular computed parameter and the brightness, intensity, or shade of the assigned color at a particular pixel may correspond to the value of the particular harmonic frequency echo signal and/or computed parameter associated with the assigned color at the location represented by the particular pixel. Multiple harmonic frequency echo signals and/or computed parameters may be displayed on the image using multiple colors.

One or more of the generated images may be displayed together on display 122. Additionally or alternatively, the user may toggle between the generated images using a selection item (e.g., button, etc.) displayed on display 122, a gesture on the touchscreen associated with display 122, a button on control unit 120 or ultrasound probe 110, a voice command, and/or using another selection method.

Additionally or alternatively, the echo frequency components or computed parameters may be provided as inputs to a classifier (block 575) and the classifier output may be used to characterize the area of interest (block 585). For example, the generated images may be provided to classifier 440 that has been trained to characterize the area of interest. For example, classifier 440 may be trained to identify a particular target (e.g., organ, fluid type, structure, tissue, medical instrument, ultrasound artifact, etc.); to distinguish a first target (e.g., organ, fluid type, structure, tissue, medical instrument, type of ultrasound artifact, etc.) from a second target; to identify a boundary between a first target (e.g., organ, fluid type, structure, tissue, medical instrument, ultrasound artifact, etc.) and a second target; to distinguish a fluid area from a non-fluid area; and/or to otherwise characterize a particular area of interest. Classifier 440 may, for example, generate an image that identifies pixels classified into a first class with a first value (e.g., a dark shading) and pixels classified into a second class with a second value (e.g., a light shading). Furthermore, classifier 440 may be trained to distinguish between three or more different targets (e.g., organs, fluid types, structures, tissues, medical instruments, ultrasound artifacts, etc.) and may generate an image that identifies pixels classified into one of a set of classes, where each class corresponds to a different type of target. For example, each type of target may be associated with a different color, different shading intensity, different fill patterns, etc. Additionally, each type of target may be labeled with a label that identifies the type of target.

Figure 6:
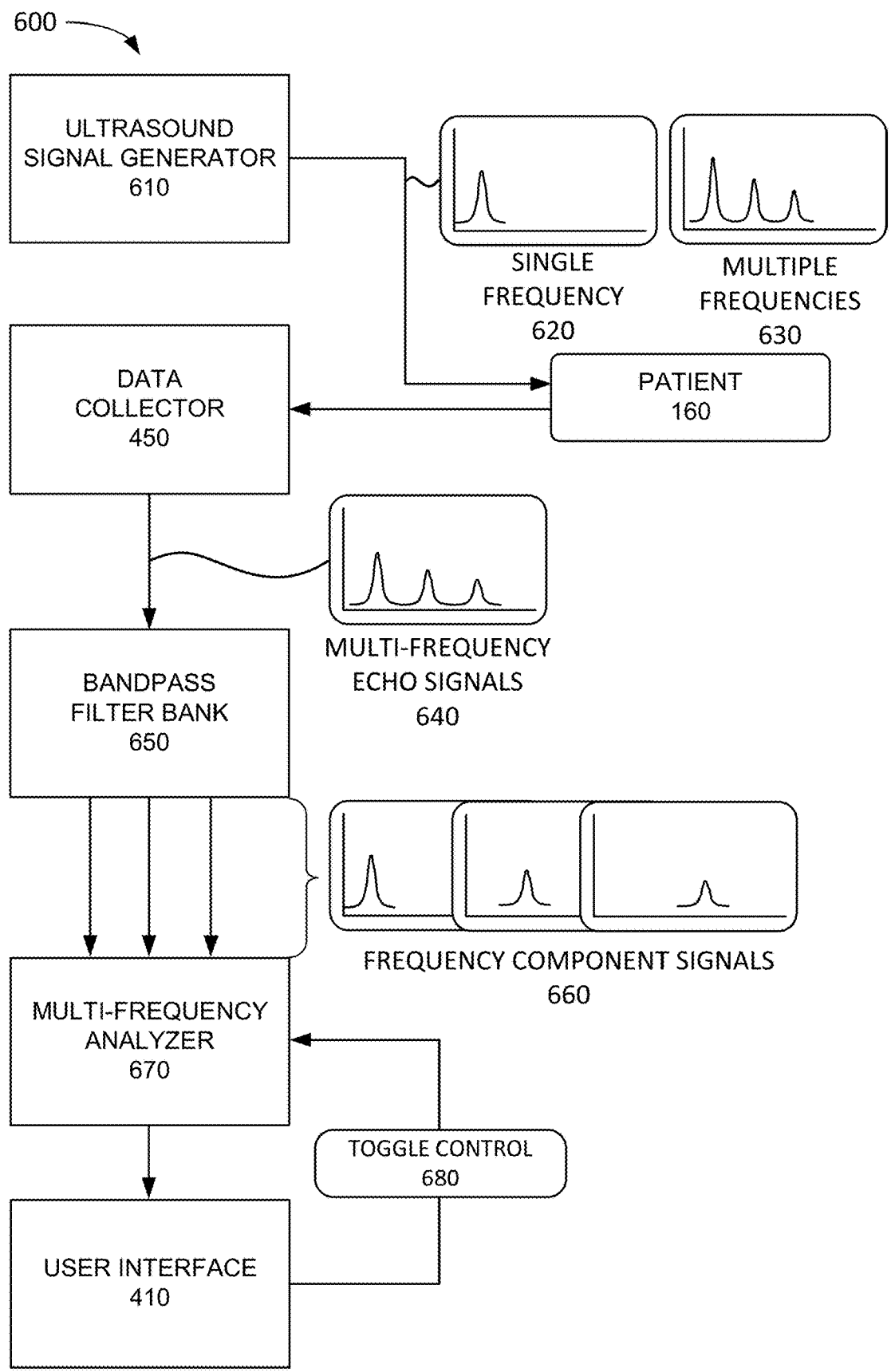
FIG. 6 is a diagram of a first exemplary multiple frequency ultrasound scanning implementation.

FIG. 6 is a diagram of a first exemplary multiple frequency ultrasound scanning implementation 600. As shown in FIG. 6, in implementation 600, multiple harmonic frequency signals are transmitted along with a fundamental frequency. An ultrasound signal generator 610 may generate an ultrasound pulse at a single frequency 620 or at multiple frequencies 630. For example, in order to generate multiple frequencies 630, ultrasound signal generator 610 may include multiple transducers, with each transducer configured to generate an ultrasound pulse at a particular frequency. For example, the multiple transducers may generate pulses at a fundamental frequency and one or more (integer or non-integer) harmonics of the fundamental frequency. Ultrasound signal generator 610 may include an excitation pulse generator, a set of transducers, and controlling electronics. Frequency manager 420 may select which ultrasound transducers are activated during a particular data collection event. The generated ultrasound pulses may be transmitted into patient 160. Data collector 450 may include receiver circuitry coupled to the transducers to obtain echo signals from ultrasound signal generator 610 that include multi-frequency harmonic echo signals 640 and may provide the multi-frequency harmonic echo signals 640 to a bandpass filter bank 650. Bandpass filter bank 650 may include a first bandpass filter to pass a frequency range centered around the fundamental frequency, a second bandpass filter to pass a frequency range centered around the first harmonic frequency, and a third bandpass filter to pass a frequency range centered around the second harmonic frequency. Bandpass filter bank 650 may provide frequency component signals 660 to multi-frequency analyzer 670.

Multi-frequency analyzer 670 may select particular ones of frequency component signals 660 and provide the selected frequency component signals 660 to image generator 430 (not shown in FIG. 6). Image generator 430 may generate a first image based on the fundamental frequency, a second image based on the first harmonic frequency, and a third image based on the second harmonic frequency.

Image generator 430 may provide the generated images to user interface 410 and user interface 410 may display one or more of the images on display 122. The user may use a toggle control 680, such as a button on display 122, to toggle between the generated images (see FIGS. 8 and 9).

Figure 7:
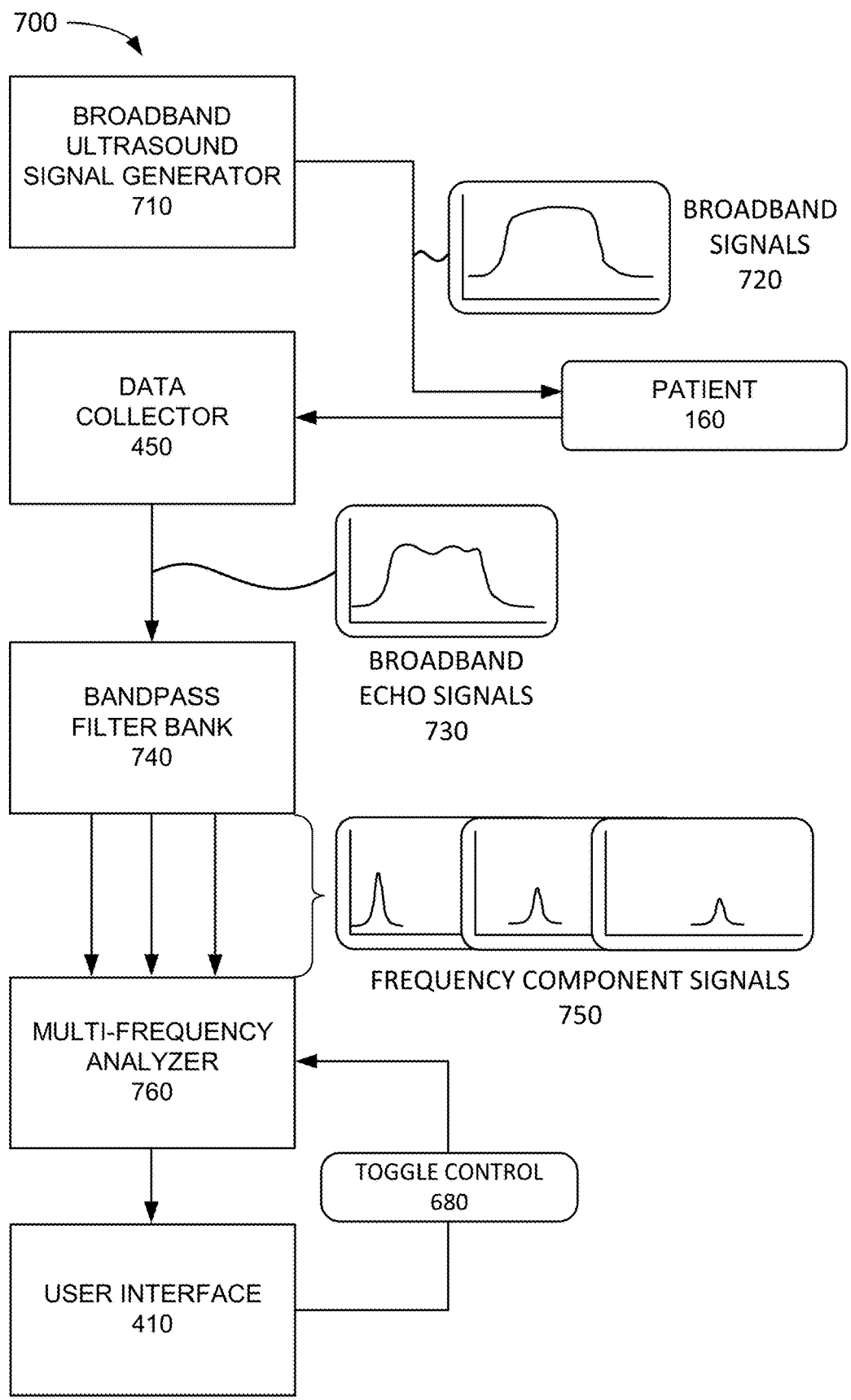
FIG. 7 is a diagram of a second exemplary multiple frequency ultrasound scanning implementation.

FIG. 7 is a diagram of a second exemplary multiple frequency ultrasound scanning implementation 700. As shown in FIG. 7, in implementation 700, broadband ultrasound signals are transmitted by transducer 260 (or transducer array 275 or 285). A broadband ultrasound signal generator 710 (e.g., implemented by frequency manager 420) may generate broadband signals 720. Broadband ultrasound signal generator 710 may include an excitation pulse generator, a broadband transducer, and controlling electronics.

The generated broadband ultrasound signals 720 may be transmitted into patient 160. Data collector 450 may obtain echo signals from patient 160 that include broadband echo signals 730 and may provide the broadband echo signals 730 to a bandpass filter bank 740. Bandpass filter bank 740 may be implemented as, for example, a set of bandpass filters, an STFT signal processor, a WD signal processor, a WPD signal processor, and/or another type of bandpass filter bank implementations, For example, bandpass filter bank 740 may be implemented as a digital signal processor configured to retrieve 128 frequency components signals 750 from harmonic echo signals 730 using an STFT operation. Frequency component signals 750 may be provided as inputs to multi-frequency analyzer 760. Multi-frequency analyzer 760 may include, for example, classifier 440 implemented as a neural net trained to detect an organ (e.g., bladder). Classifier 440 may output an image that includes pixels of a first color, brightness, or shading for areas detected by classifier 440 as corresponding to the organ and pixels of a second color, brightness, or shading for areas that do not correspond to the organ (see FIG. 10). The user may use a toggle control 680, such as a button on display 122, to toggle between different images generated by classifier 440. For example, the user may toggle between different shading or contrast levels, between different detected targets (e.g., different organs, etc.), between different detected target boundaries, etc.

Figure 8:
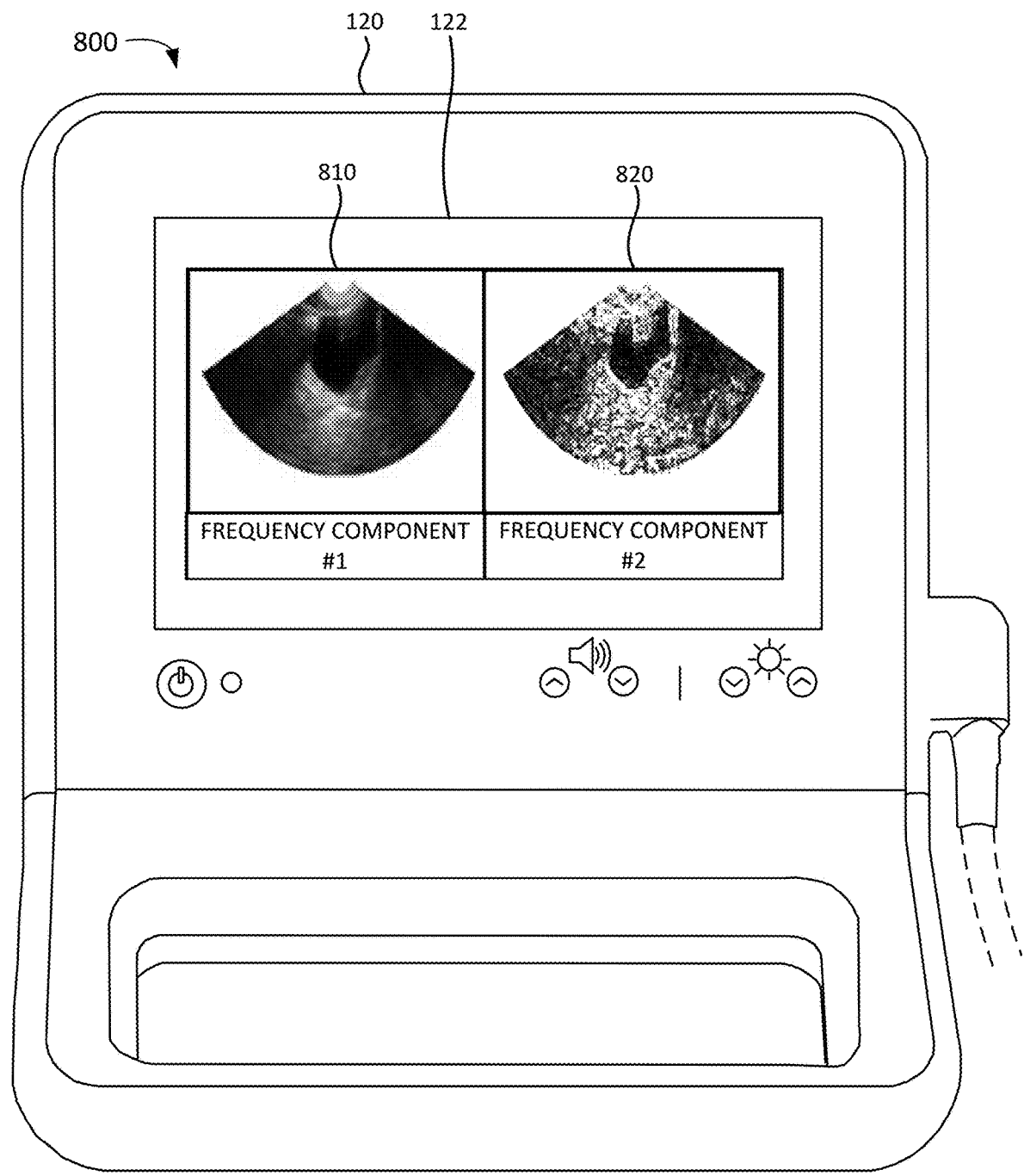
FIG. 8 is a diagram of a first user interface according to an implementation described herein.

FIG. 8 is a diagram of a first user interface 800 according to an implementation described herein. As shown in FIG. 8, in some implementations, a first ultrasound image 810 and a second ultrasound image 820 may be displayed together on display 122. First ultrasound image 810 may correspond to an image based on a first harmonic component and second ultrasound image 820 may correspond to a second harmonic component. For example, first ultrasound image 810 may correspond to a graphical representation of the power ratio between the fundamental frequency and the first harmonic frequency and second ultrasound image 820 may correspond to a graphical representation of the power ratio of the first harmonic frequency and the second harmonic frequency. While FIG. 8 illustrates a first harmonic component and a second harmonic component, other types of images based on multi-frequency ultrasound data may be generated and displayed, such as an image that combines one or more harmonic components (e.g., by adding pixel values, by averaging pixel values, etc.), an image that displays P-mode values, an image that displays a computed parameter (e.g., a power ratio between a first harmonic component and a second harmonic component, and/or any other type of image that may be generated based on multi-frequency ultrasound data.

Figure 9:
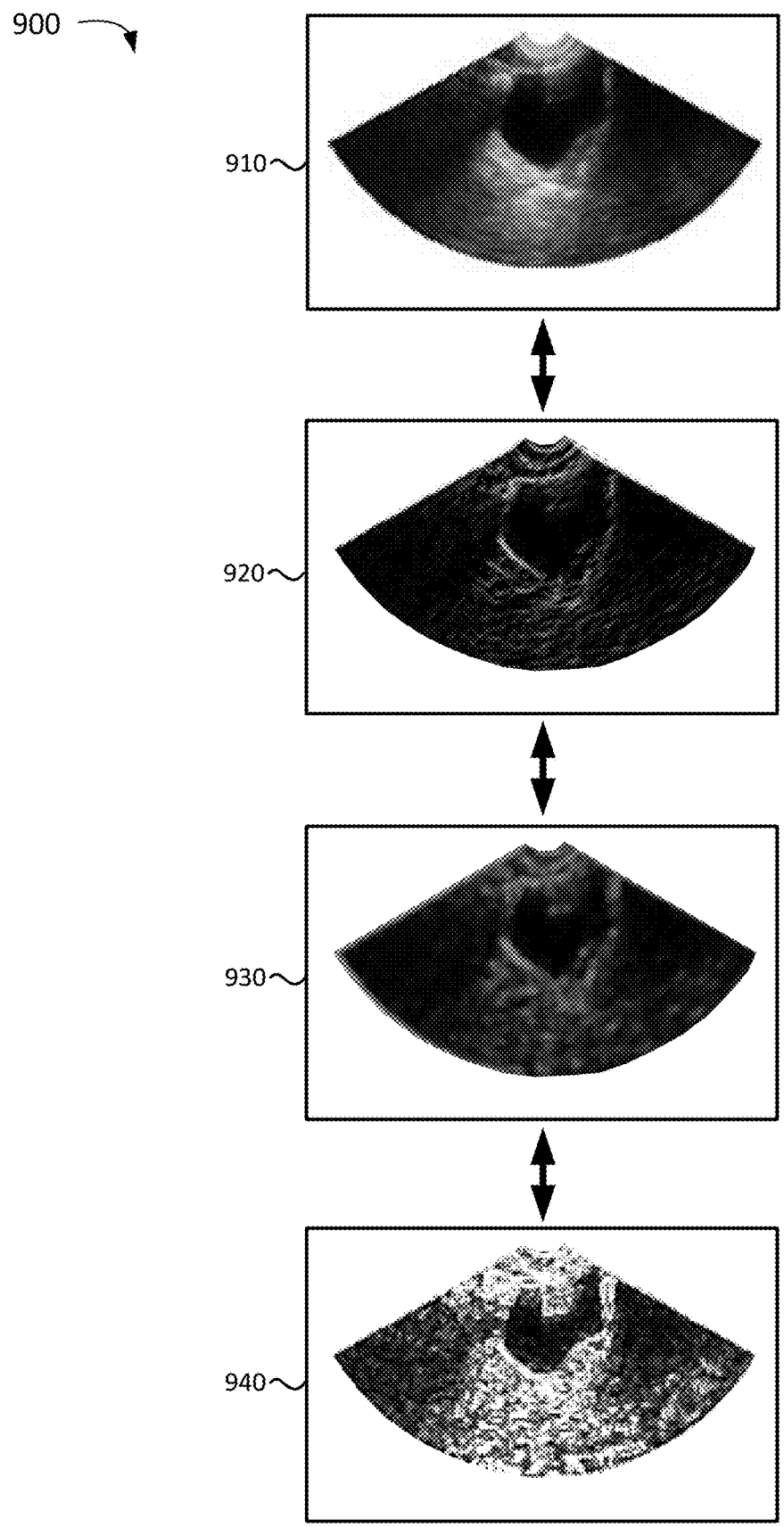
FIG. 9 is a diagram of a second user interface according to an implementation described herein.

FIG. 9 is a diagram of a second user interface 900 according to an implementation described herein. As shown in FIG. 9, second user interface 900 shows a user toggling between different images 910, 920, 930, and 940 based on retrieved harmonic components. For example, display 122 may toggle between images 910, 920, 930, and 940 as the user presses a selection object on the touchscreen associated with display 122 (and/or another key or button associated with ultrasound system 100). In yet other implementations, images 910, 920, 930, and 940 may be displayed in a tiled configuration and toggling may change which tile is moved to the front.

Figure 10:
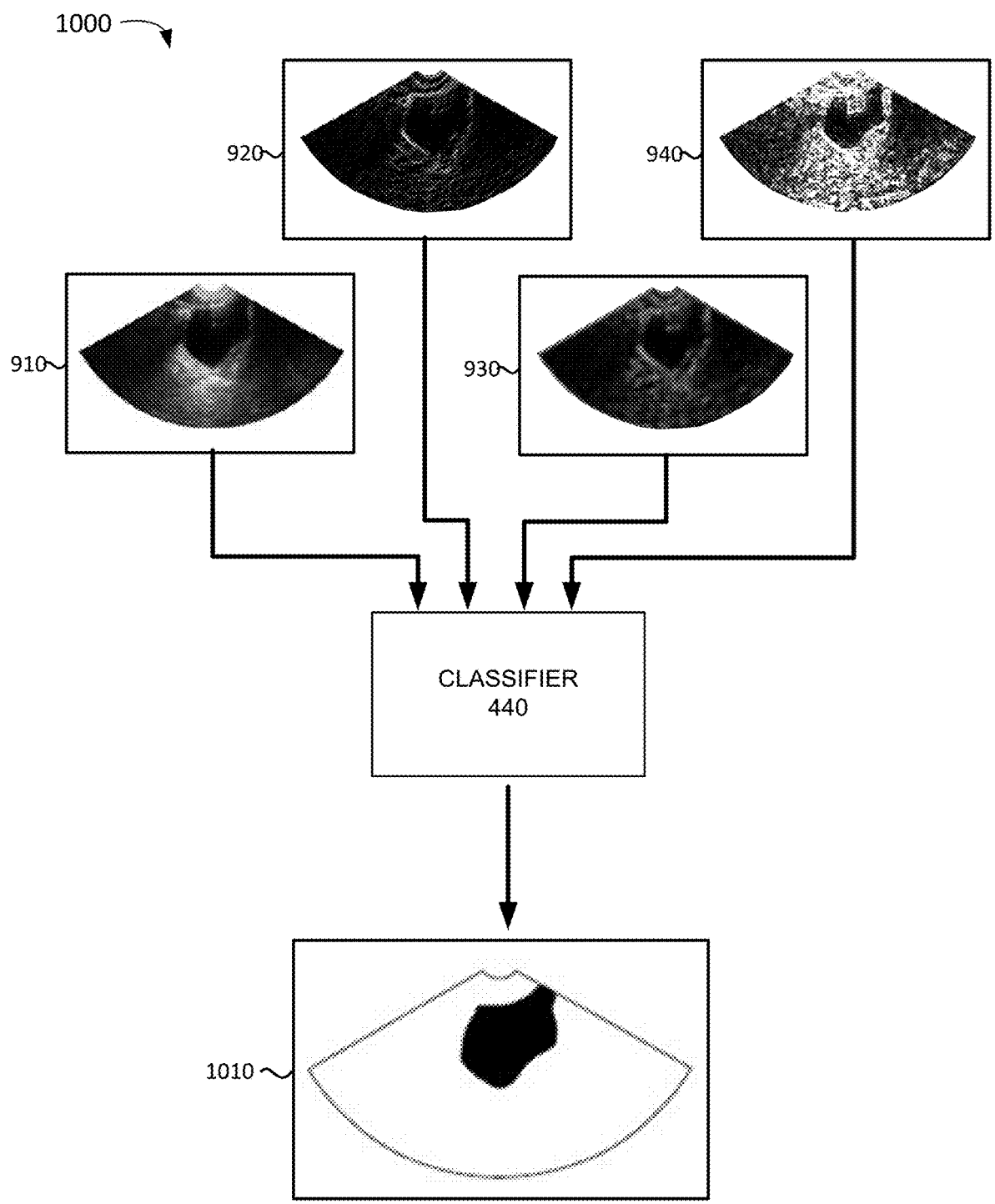
FIG. 10 is a diagram of a third user interface according to an implementation described herein.

FIG. 10 is a diagram of a third user interface 1000 according to an implementation described herein. As shown in FIG. 10, images 910, 920, 930, and 940 may be provided as inputs to classifier 440 and classifier 440 may output an image 1010 that identifies an organ in the area of interest captured in images 910, 920, 930, and 940. While FIG. 10 illustrates images 910-940 as inputs to classifier 440, the inputs to classifier 440 may not be limited to images. Classifier 440 may take as input any information derived from received multi-frequency ultrasound data, such as one or more computed parameters (e.g., power ratios, attenuation coefficients, global power level per frequency component, etc.) instead of, or in addition to, receiving as input one or more sets of image pixel data.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while a series of blocks have been described with respect to FIG. 5, the order of the blocks may be modified in other implementations. Further, non-dependent blocks may be performed in parallel.

Although embodiments described above refer to scanning a bladder, other organs, joints, vessels, and/or body areas, such as an aorta, prostate, kidney, uterus, ovaries, heart, etc., could scanned and/or imaged in other implementations. Furthermore, medical instruments, such as catheters, needles, cannulas, etc. may be scanned and/or imaged using the implementations described herein. Moreover, implementations described herein may be used to detect and identify ultrasound artifacts. Furthermore, in some implementations, obtaining an adequate aiming mode and then proceeding to a 3D scan may be automatic based on a size of an image and/or another parameter.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/ "comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a computing device, the method comprising:
   transmitting, by the computing device, ultrasound signals using an ultrasound probe toward an area of interest in a patient's body, wherein the ultrasound signals include a fundamental frequency signal and at least one harmonic frequency signal;
   receiving, by the computing device, echo signals from the area of interest based on the transmitted ultrasound signals;
   obtaining, by the computing device, a fundamental frequency echo signal and at least one harmonic frequency echo signal from the received echo signals, wherein obtaining the fundamental frequency echo signal and the at least one harmonic frequency echo signal from the received echo signals includes:
      retrieving a plurality of echo signals corresponding to the fundamental frequency echo signal and the at last one harmonic frequency echo signal using a plurality of bandpass filters;
   generating, by the computing device, at least one ultrasound image, wherein the at least one ultrasound image includes pixel values generated based on a particular one of the plurality of echo signals, or on a parameter computed based on the particular one of the plurality of echo signals;
   providing, by the computing device, the generated at least one ultrasound image as an input into a classifier to characterize the area of interest, wherein the classifier is trained to receive inputs that include at least one ultrasound image that includes pixel values generated based on a harmonic frequency component extracted from ultrasound echo signals or generated based on one or more parameters computed based on the harmonic frequency component, and generate, based on the received inputs, an output that characterizes a target in the area of interest; and generating, by the computing device, a visual representation of the area of interest based on the obtained fundamental frequency echo signal and the obtained at least one harmonic frequency echo signal, or based on the characterized area of interest.

2. The method of claim 1, wherein transmitting the ultrasound signals using an ultrasound probe includes:
transmitting a broadband ultrasound signal.

3. The method of claim 1, wherein the at least one harmonic frequency signal includes a non-integer harmonic signal.

4. The method of claim 1, wherein obtaining the fundamental frequency echo signal and the at least one harmonic frequency echo signal from the received echo signals further includes:
retrieving an echo signal corresponding to a non-integer harmonic of the fundamental frequency.

5. The method of claim 1, wherein retrieving the plurality of echo signals includes performing at least one of:
a Short-Time Fourier Transform (STFT) operation,
a Wavelet Decomposition (WD), or
a Wavelet Packet Decomposition (WPD) operation.

6. The method of claim 1, wherein generating the visual representation of the area of interest includes:
generating a plurality of ultrasound images, wherein a particular one of the plurality of ultrasound images is based on a particular one of the plurality of echo signals.

7. The method of claim 1, wherein the classifier is trained to at least one of:
distinguish between a first target and a second target in the area of interest based on the plurality of echo signals,
identify an area that includes a target in the area of interest based on the plurality of echo signals, or
identify a target boundary in the area of interest based on the plurality of echo signals.

8. The method of claim 1, further comprising:
calculating a plurality of parameters based on the plurality of echo signals.

9. The method of claim 8, wherein generating the visual representation of the area of interest includes:
generating a plurality of ultrasound images, wherein a particular one of the plurality of ultrasound images is based on a particular one of the plurality of parameters.

10. The method of claim 8, wherein generating the visual representation of the area of interest includes:
providing a plurality of power ratios as inputs into the classifier, wherein the classifier is trained to at least one of:
distinguish between a first target and a second target in the area of interest based on the plurality of power ratios,
identify an area that includes a target in the area of interest based on the plurality of power ratios, or
identify a target boundary in the area of interest based on the plurality of power ratios.

11. A system comprising:
an ultrasound probe; and
a controller unit configured to:
communicate with the ultrasound probe;
transmit ultrasound signals via the ultrasound probe toward an area of interest in a patient's body, wherein the ultrasound signals include a fundamental frequency signal and at least one harmonic frequency signal;
receive echo signals from the area of interest based on the transmitted ultrasound signals;
obtain a fundamental frequency echo signal and at least one harmonic frequency echo signal from the received echo signals, wherein, when obtaining the fundamental frequency echo signal and the at least one harmonic frequency echo signal from the received echo signals, the controller unit is further configured to:
retrieve a plurality of echo signals corresponding to the fundamental frequency echo signal and the at last one harmonic frequency echo signal using a plurality of bandpass filters;
generate at least one ultrasound image, wherein the at least one ultrasound image includes pixel values generated based on a particular one of the plurality of echo signals, or on a parameter computed based on the particular one of the plurality of echo signals;
provide the generated at least one ultrasound image as an input into a classifier to characterize the area of interest, wherein the classifier is trained to receive inputs that include at least one ultrasound image that includes pixel values generated based on a harmonic frequency component extracted from ultrasound echo signals or generated based on one or more parameters computed based on the harmonic frequency component, and generate, based on the received inputs, an output that characterizes a target in the area of interest; and
generate a visual representation of the area of interest based on the obtained fundamental frequency echo signal and the obtained at least one harmonic frequency echo signal, or based on the characterized area of interest.

12. The system of claim 11, wherein, when transmitting the ultrasound signals via the ultrasound probe, the controller unit is configured to at least one of:
transmit a broadband ultrasound signal, or
transmit at least one non-integer harmonic signal.

13. The system of claim 11, wherein, when generating the visual representation of the area of interest, the controller unit is further configured to:
generate a plurality of ultrasound images, wherein a particular one of the plurality of ultrasound images is based on a particular one of the plurality of echo signals.

14. The system of claim 11, wherein the classifier is trained to at least one of:
distinguish between a first target and a second target in the area of interest based on the plurality of echo signals,
identify an area that includes a target in the area of interest based on the plurality of echo signals, or
identify a target boundary in the area of interest based on the plurality of echo signals.

15. The system of claim 11, wherein the controller unit is further configured to:
calculate a plurality of parameters based on the plurality of echo signals.

16. The system of claim 15, wherein, when generating the visual representation of the area of interest, the controller unit is further configured to:
generate a plurality of ultrasound images, wherein a particular one of the plurality of ultrasound images is based on a particular one of the plurality of parameters.

17. The system of claim 15, wherein, when generating the visual representation of the area of interest, the controller unit is further configured to:

provide the plurality of parameters as inputs into the classifier, wherein the classifier is trained to at least one of:
- distinguish between a first target and a second target in the area of interest based on the plurality of parameters,
- identify an area that includes a target in the area of interest based on the plurality of parameters, or
- identify a target boundary in the area of interest based on the plurality of parameters.

18. A device comprising:
logic configured to:
- transmit ultrasound signals via an ultrasound probe toward an area of interest in a patient's body, wherein the ultrasound signals include a fundamental frequency signal and at least one harmonic frequency signal, wherein the fundamental frequency signal and the at least one harmonic frequency signal are transmitted sequentially;
- receive echo signals from the area of interest based on the transmitted ultrasound signals;
- obtain a fundamental frequency echo signal and at least one harmonic frequency echo signal from the received echo signals, wherein, when obtaining the fundamental frequency echo signal and the at least one harmonic frequency echo signal from the received echo signals, the logic is further configured to:
  - retrieve a plurality of echo signals corresponding to the fundamental frequency echo signal and the at last one harmonic frequency echo signal;
- generate at least one ultrasound image, wherein the at least one ultrasound image includes pixel values generated based on a particular one of the plurality of echo signals, or on a parameter computed based on the particular one of the plurality of echo signals;
- provide the generated at least one ultrasound image as an input into a classifier to characterize the area of interest, wherein the classifier is trained to receive inputs that include at least one ultrasound image that includes pixel values generated based on a harmonic frequency component extracted from ultrasound echo signals or generated based on one or more parameters computed based on the harmonic frequency component, and generate, based on the received inputs, an output that characterizes a target in the area of interest; and
- generate a visual representation of the area of interest based on the obtained fundamental frequency echo signal and the obtained at least one harmonic frequency echo signal, or based on the characterized area of interest.

19. A method performed by a computing device, the method comprising:
- transmitting, by the computing device, ultrasound signals using an ultrasound probe toward an area of interest in a patient's body, wherein the ultrasound signals include a fundamental frequency signal and at least one harmonic frequency signal;
- receiving, by the computing device, echo signals from the area of interest based on the transmitted ultrasound signals;
- obtaining, by the computing device, a fundamental frequency echo signal and a harmonic frequency echo signal from the received echo signals;
- generating, by the computer device, a first ultrasound image that includes pixel values generated based on the obtained fundamental frequency echo signal;
- generating, by the computer device, a second ultrasound image that includes pixel values generated based on a ratio of the obtained fundamental frequency echo signal and the obtained harmonic frequency echo signal computed for particular pixel positions;
- providing, by the computing device, the generated first ultrasound image and the generated second ultrasound image as an input into a classifier to perform a segmentation of the area of interest; and
- generating, by the computing device, a visual representation of the area of interest based on the segmentation of the characterized area of interest.

* * * * *